Figure 1:
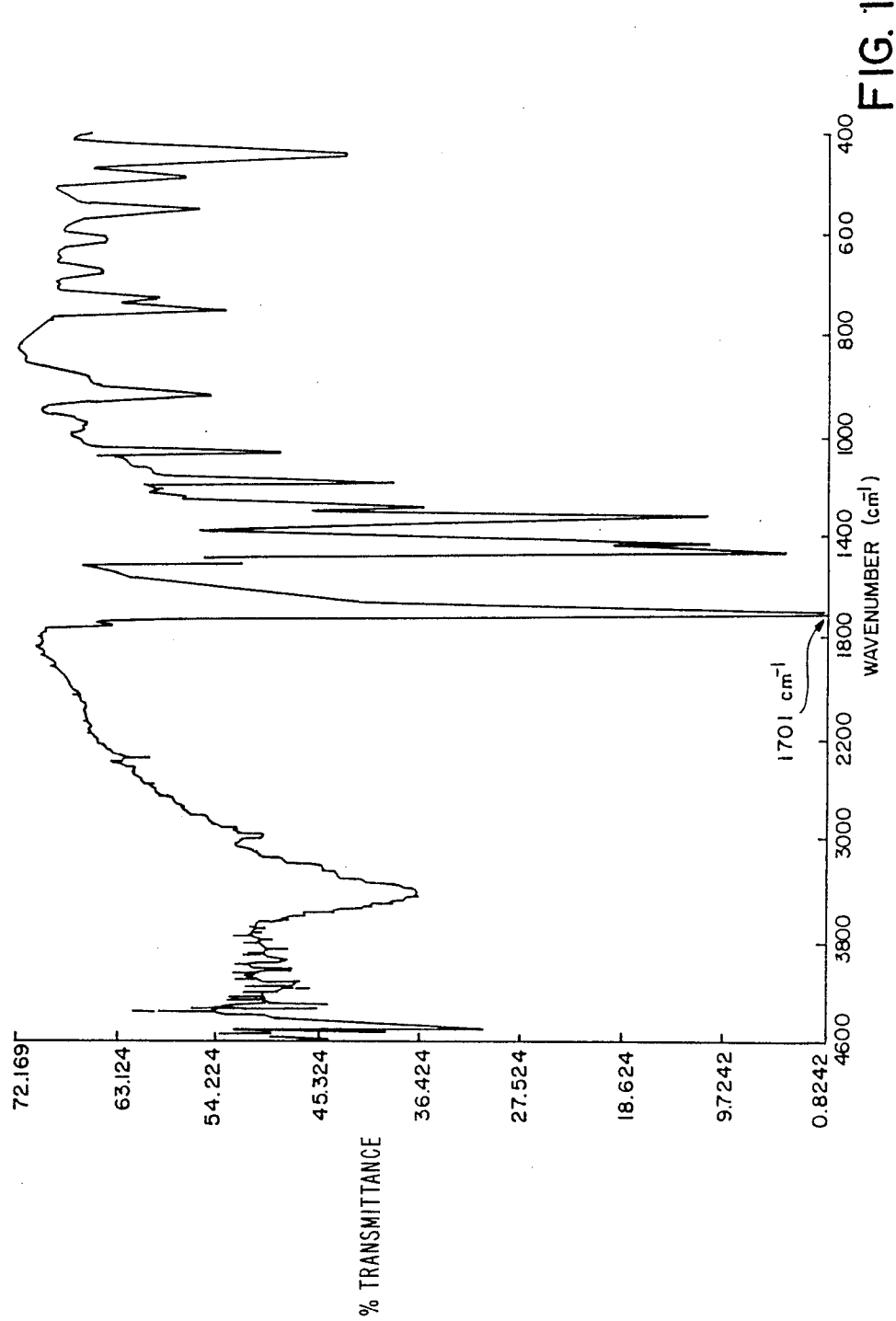

United States Patent [19]

Herzlinger et al.

[11] Patent Number: 4,977,262

[45] Date of Patent: Dec. 11, 1990

[54] TRISUBSTITUTED SYMMETRICAL TRIAZINES

[75] Inventors: Andrei Herzlinger, Karmiel; Leonard M. Shorr, Haifa; Salomone Antebi, Haifa; Theodor Morel-Fisher, Haifa; Lev Utevskii, Beer-Sheva; Yaakov Scheinert, Omer, all of Israel

[73] Assignee: Bromine Compounds Limited, Israel

[21] Appl. No.: 236,557

[22] Filed: Aug. 25, 1988

[30] Foreign Application Priority Data

Aug. 28, 1987 [IL] Israel .................................. 83679

[51] Int. Cl.$^5$ .................. C07D 251/12; C07D 251/30; B05D 3/02; C09D 5/16
[52] U.S. Cl. ................................ 544/221; 544/219; 427/389.8; 427/393.3; 427/393.5; 106/18.21
[58] Field of Search ......................................... 544/221

[56] References Cited

U.S. PATENT DOCUMENTS 4,602,080 7/1986 Lambert et al. .................... 544/221

Primary Examiner—Mary C. Lee
Assistant Examiner—J. Richter
Attorney, Agent, or Firm—Lerner, David, Littenberg, Krumholz & Mentlik

[57] ABSTRACT

Triazine derivatives of the formula:

$$[(NCO)_3R_1R_2R_3]_n \qquad (I)$$

are described, wherein:

$R_1$, $R_2$ and $R_3$ are the same or different and represent a ring perhalogenated benzyl and/or xylylidene, and which are bonded to the triazine ring on the N atoms when the ring is saturated, or on the O atoms when the ring is unsaturated, and n is an integer between 1 and 5. The invention is further directed to flame-retardant compositions and to plastic compositions which comprise a compound of formula I.

5 Claims, 4 Drawing Sheets

TRISUBSTITUTED SYMMETRICAL TRIAZINES

BACKGROUND OF THE INVENTION

1. The Field of the Invention

The present invention relates to novel trisubstituted symmetrical triazines, to processes for their preparation, and to their use as flame-retardant agents in synthetic resins. More particularly, the invention relates to derivatives of 2,4,6-trihydroxy-s-triazine, which contain ring-halogenated moieties.

2,4,6-Trihydroxy-s-triazine may exist in two limiting forms: the enol form (cyanuric acid) and the triketo form, known as isocyanuric acid-as well as in two intermediate mono- and di-keto forms. Isocyanuric acid exists in acidic solutions (below pH 6), and is completely enolized to cyanuric acid in strong basic solutions.

2. The Prior Art

Numerous mono-, di- and trisubstitued organic derivatives of cyanuric acid and of isocyanuric acid are known in the art, most of which are obtained from cyanuric chloride or by the trimerization of isocyanates, rather than from cyanuric acid. Attempts to obtain cyanurate esters directly or by means of alkali salts of cyanuric acid have been unsuccessful, and only the isocyanurate esters were so obtained [Smolin, E. M. and Rapoport, L., "The Chemistry of Heterocyclic Compounds", A. Weissberger Ed., Interscience, New York 1959, vol. 13, pp 1–48; Kirk-Othmer, Encyclopedia of Chemical Technology, 3rd ed., Vol. 7, p. 400 (John Wiley & Sons, 1979)]. Instead of cyanurates, esters of isocyanuric acid are isolated when agents such as benzyl and alkyl chlorides are used.

The art is constantly searching for new and improved flame-retardant agents, to meet the ever increasing safety and health requirements and to improve the quality of the resulting plastic compositions and their processability. Halogen-containing compounds are commonly used for this application in one of two forms: as active fire-retardants or as simple additives to the polymeric material. An active fire retardant is defined as being chemically incorporated into the polymeric structure by formal chemical bonds. Simple additives are not chemically bonded but are simply dissolved and/or dispersed in the polymer matrix. The compounds of the invention are primarily directed to be used as simple additives to a variety of plastic materials.

Halogen containing fire (or flame) retardant materials (FRs), and particularly brominated FRs, often suffer from low thermal stability, which causes serious disadvantages. The release of acidic vapors, for instance, is usually accompanied by the discoloration of the plastic article during molding operations and further causes the corrosion of processing equipment. Additionally, polymeric compositions comprising halogenated FRs usually have enhanced sensitivity to UV radiation, which gives rise to accelerated product deterioration.

Because of compatibility problems, FR additives commonly are fugitive, viz., they are lost from the polymer matrix either during processing or during ageing of the finished product, or both. This can take place because of vaporization, bleeding of incompatible materials or the leaching of soluble additives. One such effect is known as "blooming", and may also render the product inacceptable because of the appearance of a powder of FR material on the surface of the object. This, of course, also diminishes the concentration of the active FR material within the polymeric matrix. These problems are particularly felt in connection with high performance plastics, i.e., those plastic materials intended for use under high stress conditions, such as high temperatures, which also require high temperatures for processing.

Employing polymeric FR additives to overcome fugitivity has not been entirely successful. Mark's Encyclopedia of Polymer Science and Technology [Vol. 7, Interscience Publishers, p. 19] cites among the serious disadvantages which limit the use of halogen-containing polymers as FRs, especially in thermoplastic molding compounds: (a) The halogen content of the polymer is usually of such a low level that massive amounts of polymer are required to obtain the desired flame-retardancy; (b) The low thermal stability of the halogen-containing polymer often limits processing to unrealistically low temperatures; and (c) Expensive processing techniques may be required for suitable blending of the two polymers.

SUMMARY OF THE INVENTION

It is therefore an object of the present invention to provide novel trisubstituted symmetrical triazines which can be usefully exploited as flame-retardant agents in synthetic resins.

It is a further object of the invention to provide plastic compositions comprising said trisubstituted symmetrical triazines as flame-retardant agents, alone or in admixture with other flame-retardant agents and/or other additives useful in plastics.

The compounds according to the invention are novel compounds of the formula:

$$[(NCO)_3R_1R_2R_3]_n \quad (I)$$

wherein:

$R_1$, $R_2$ and $R_3$ are the same or different and represent a ring perhalogenated benzyl and/or xylylidene, and which are bonded to the triazine ring on the N atoms when the ring is saturated, or on the O atoms when the ring is unsaturated, and n is an integer between 1 and 5.

Preferred compounds of formula I are the trisubstituted symmetrical triazines of the formula $$(NCO)_3R_1R_2R_3$$

wherein:

$R_1$, $R_2$ and $R_3$ are the same or different and represent a ring perhalogenated benzyl, and which are bonded to the triazine ring on the N atoms when the ring is saturated, or on the O atoms when the ring is unsaturated.

According to a preferred embodiment of the invention, the compound of formula I is an isocyanurate of the formula

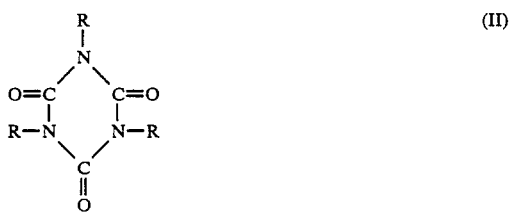

(II)

wherein R is in all cases the same or different, and represents a ring perhalogenated benzyl According to another preferred embodiment of the invention, the compound of formula I is a derivative of cyanuric acid having the formula

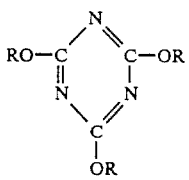 (III)

wherein R is in all cases the same or different, and represents a ring perhalogenated benzyl.

Preferably, R in the above formulas (II) and (III) is selected from pentabromobenzyl and pentachlorobenzyl. A most preferred compound of the invention is that which is trisubstituted by pentabromobenzyl.

Polymeric materials of the formula:

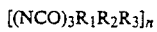

wherein:

$R_1$, $R_2$ and $R_3$ are the same or different and represent a ring perhalogenated benzyl and/or xylylidene, and which are bonded to the triazine ring on the N atoms when the ring is saturated, or on the O atoms when the ring is unsaturated, and n is an integer between 2 and 5 are also novel compounds, also useful as FRs, and as such they also from part of the invention. An example of such a polymeric compound of the invention is Poly(N-pentabromobenzyl-N', N"-tetrabromoxylylidene isocyanurate.

The invention is also directed to flame-retardant compositions comprising as an active agent a compound of the formula

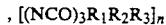

wherein:

n is an integer comprised between 1 and 5;

$R_1$, $R_2$ and $R_3$ are the same or different and represent a ring perhalogenated benzyl and, when n is greater than 1, a ring perhalogenated benzyl and/or xylylidene, and which are bonded to the triazine ring on the N atoms when the ring is saturated, or on the O atoms when the ring is unsaturated; alone or in admixture with other flame retardants and/or other additives usable in plastics.

Examples of suitable active agent are Tris(pentachlorobenzyl) isocyanurate, Tris(pentabromobenzyl) cyanurate, Tris(pentachlorobenzyl)cyanurate, Tris(pentabromobenzyl) isocyanurate and Poly(N-pentabromobenzyl-N', N"-tetrabromoxylylidene isocyanurate.

Also encompassed within the present invention are plastic compositions comprising a polymer and a compound of the formula

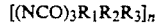

wherein:

n is an integer comprised between 1 and 5;

$R_1$, $R_2$ and $R_3$ are the same or different and represent a ring perhalogenated benzyl and, when n is greater than 1, a ring perhalogenated benzyl and/or xylylidene, and which are bonded to the triazine ring on the N atoms when the ring is saturated, or on the O atoms when the ring is unsaturated; alone or in admixture with other flame retardants and/or other additives usable in plastics.

Preferred polymers to which flame retardant properties can be usefully imparted are, e.g., acrylonitrile-butadiene-styrene and saturated or unsaturated polyester resins.

The compounds of the invention can be usefully employed as the sole flame-retardant agent in plastic compositions. However, in many cases it may be convenient to employ, in plastic compositions containing the compounds of the invention, also other known flame-retardant and/or flame-retardant synergistic compounds, such as organo-phosphorous compounds, zinc borate, oxides, sulfides or organic salts of antimony, arsenic or boron, aluminium trihydrate, or the like.

Conventional additives useful in plastic compositions, such as fillers, pigments, smoke suppressors, lubricants, plasticizers and the like, may of course also be incorporated in plastic compositions containing the compounds of the invention.

EXAMPLE 1

Tris(pentabromobenzyl)isocyanurate.

(A) Preparation of Tris(pentabromobenzyl)isocyanurate.

(a) Preparation of the trisodium salt of cyanuric acid

To a solution of NaOH (60 g, 1.5 mol) in $H_2O$ (750 ml), cyanuric acid (CA) (64.5 g, 0.5 mol) was added during about 10 minutes. The solution was purified by filtering trough glass wool. The water was evaporated and a white solid (96.6 g, 0.49 mol) was obtained in 99% yield. The salt was dried at 110° C. overnight. Analysis, calcd. for $C_3N_3Na_3O_3$: Na 35.36%; N 21.54%. Found: Na 34.8%; N 21.25%. By Karl-Fischer analysis it was found that 0.9% of $H_2O$ was retained by the solid.

Similarly, the salt was prepared also from an ethanolic solution using the same reactant ratio as above. Cyanuric acid was added to a hot, freshly prepared, NaOH ethanolic solution and the reaction mixture was left stirring overnight at room temperature. The precipitate was filtered and washed with cold ethanol and the crystalline solid was dried and collected in 96% yield.

(b) Preparation from the trisodium salt.

A four-necked flask was supplied with a mechanical stirrer, a reflux condenser, separatory funnel and thermocouple. Pentabromobenzylbromide (PBB) (340 g; 0.6 mol) was dissolved at 90° C. in 1.1 l dimethylformamide (DMF) dried beforehand on molecular sieves 4 A. Thereafter 39 g (0.2 mol) of the trisodium salt of cyanuric acid were added. The yellow reaction mixture was allowed to stir overnight at 90°-95° C., after which the solution was filtered, washed with DMF and dried. A sample of this solution was titrated with $AgNO_3$ to determine $Br^-$ content (82% of the expected $Br^-$ was present).

The product, a white solid, was dried at 125°-140° C. overnight. The recovery of the product (261 g; 0.165 mol) was 82% of the theoretical yield. The solid was purified by extraction with hot toluene, to remove impurities found in the analyses, with a final yield of 79% after purification (250 g; 0159 mol).

Figure 2:
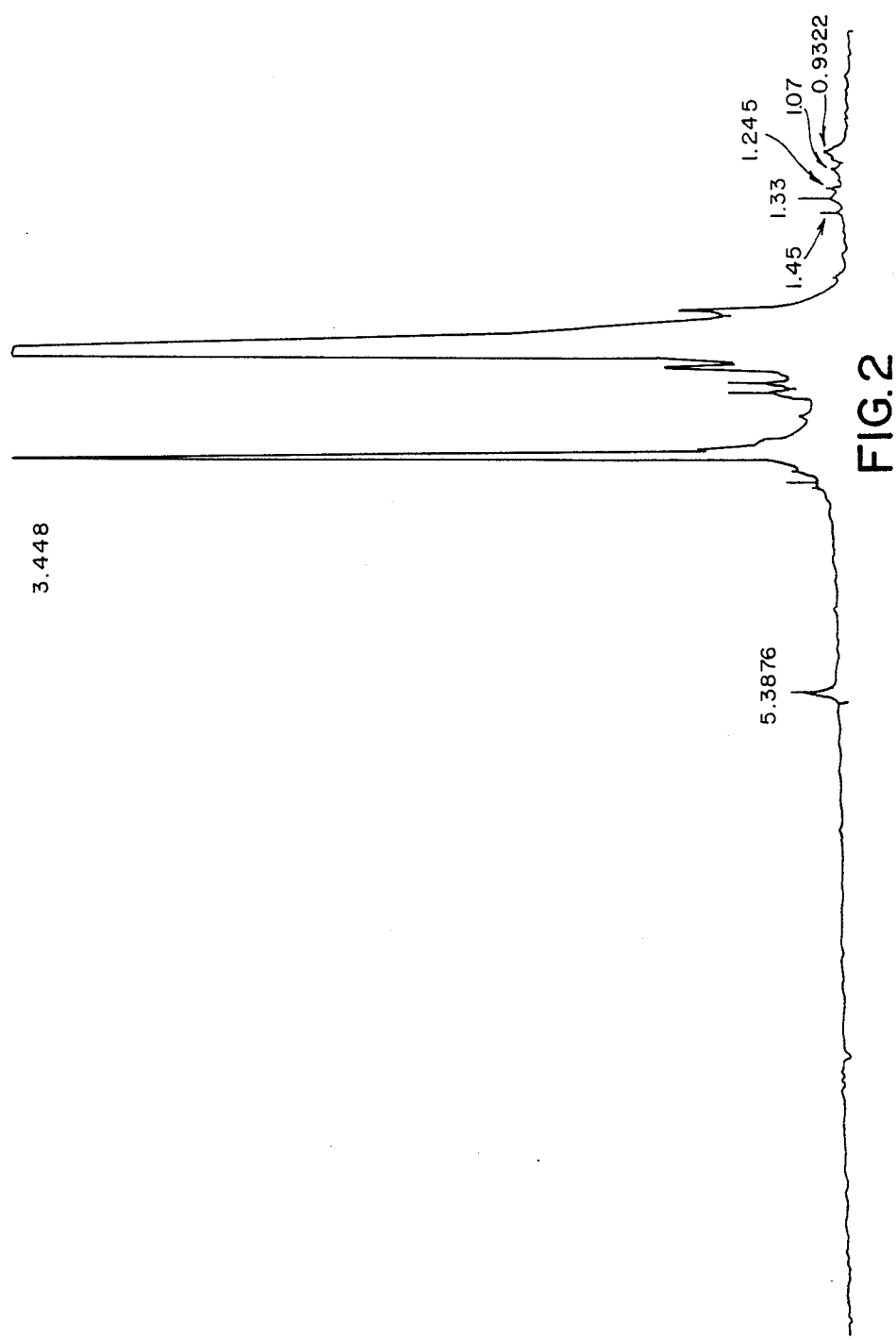

The IR (KBr) spectrum, shown in FIG. 1, showed a strong carbonyl absorption at 1701 $cm^{-1}$. The nmr spectrum (in DMSO), shown in FIG. 2, showed a peak at 5.37, belonging to the benzylic group. Shifts were calculated using TMS as an external standard. Elemental analysis was consistent with the formula of tris(pentabromobenzyl)isocyanurate.

Analysis calcd.: N 2.65%; Br 75.72%. Found: N 2.7%; Br 75.1%.

The Thermal Gravimetric Analysis of the solid product was: 1%/350° C.; 5%/382° C.; 50%/407° C.; with a major peak at 412° C.

EXAMPLE 2

Preparation of Tris(pentachlorobenzyl)cyanurate.

To 18.4 g of toluene there was added 1 g of $Al_3Cl_3$, and the mixture was heated to 75° C., after which 165 g of sulphuryl chloride, to which 1.5 g of sulfur chloride had been added, was added to the mixture during 3 hours. Heating was continued for another 30 minutes. The product was partitioned between 250 ml of toluene and 15 ml of water at the same temperature. Pentachlorotoluene (35 g), having a melting point of 216°-218° C. after recrystallization, was recovered from the organic layer.

The product obtained above was mixed with 18 g of N-bromosuccinimide and a catalytic quantity of dibenzoyl peroxide in 1 liter of $CCl_4$, under reflux, during two hours. By fractional crystallization from toluene, 25 g of pentachlorobenzyl bromide were obtained. M.p. of the product: 114°-115° C.; reported: 116° C.

A solution of 20.7 g of pentachlorobenzyl bromide in 300 ml DMF containing 30 ml of water was heated at reflux for two hours. On dilution with water solids precipitated. The solid was filtered out and washed on the filter until the wash water was free of bromide ions. On drying, 15.2 g of pentachlorobenzyl alcohol of m.p. 193°-195° C. were obtained.

Cyanuric chloride (1.84 g, 0.01 mole) and 8.7 g (0.031 mole) of pentachlorobenzyl alcohol were added to 100 ml of trichlorobenzene and heated to reflux. After 1 hour, powdered dry sodium hydroxide (1.2 g) was added portionwise over an additional period of 2 hours. The reaction mixture was then left to cool to room temperature with stirring. The solid was filtered out and washed, first with ether and then with water until the filtrate was free of chloride ions, and then dried.

Elemental analysis. Clcd.: 58% Cl and 4.6% N; Found: 57.1% Cl and 4.7% N.

EXAMPLE 3

Preparation of Tris(pentabromobenzyl) cyanurate

Pentabromobenzyl alcohol (m.p. 265°-266° C.) is prepared by the method of Tanaseichuk et al., and condensed with cyanuric chloride. The title material was prepared in a manner analogous to that described in Example 2 for the chloro-analog.

Elemental analysis: Clcd: 75.1% Br and 2.7% N; Found: 74.6% Br and 2.58% N.

EXAMPLE 4

Preparation of Tris(pentachlorobenzyl)isocyanurate.

0.1 Mole of the title material were prepared from pentachlorobenzyl chloride and the trisodium salt of cyanuric acid, following the procedure of Example 1.

Figure 3:
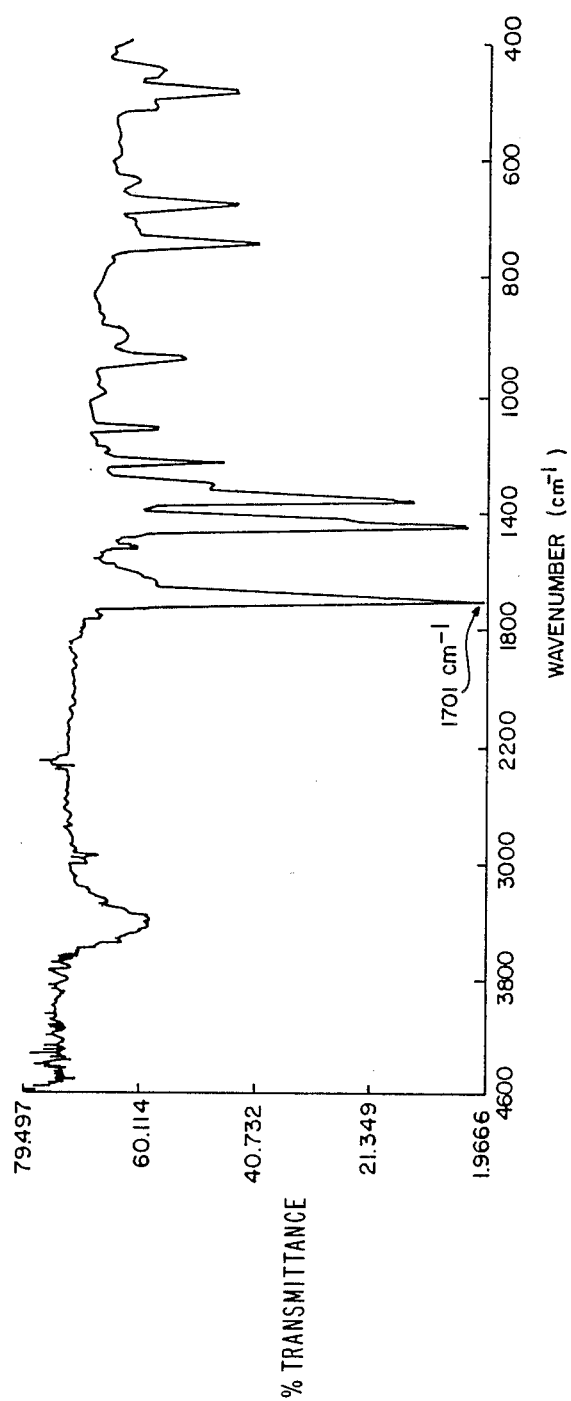
Figure 4:
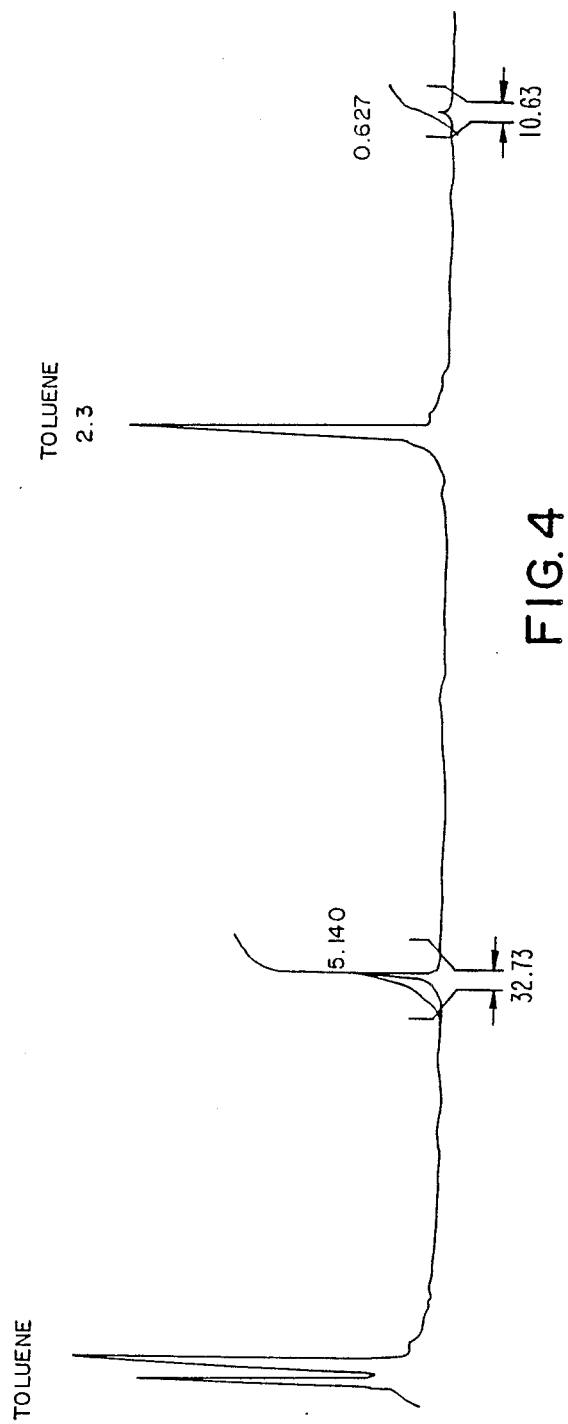

Elemental analysis - Clcd.: 58% Cl; 4.6% N. Found: 56.5% Cl; 4.4% N. The major weight loss peak as shown in the TGA of the product was at 462° C. The IR (KBr) spectrum of the product is shown in FIG. 3, and the nmr spectrum (toluene $d^8$) in FIG. 4.

EXAMPLE 5

Preparation of Poly(N-pentabromobenzyl-N', N" tetrabromoxylylidene isocyanurate)

The title compound was synthesized according to Example 1, with the exception that an equivalent mixture of 170 g (0.3 mole) of pentabromobenzyl bromide and 174 g (0.3 mole) of tetrabromoxylilydene dibromide were used instead of the 340 g of pentabromobenzyl bromide used in Example 1.

Elemental analysis: Clcd.: 69.8% Br and 4.1% N; Found: 70.2% Br and 3.9% N.

The Thermal Gravimetric Analysis of the solid product was: 2%/275° C.; 5%/337° C.; 10%/375° C. (under air, heating rate: 10° C./minute).

The following examples of preparations illustrate the use of the compounds of the invention as flame-retardant agents. The data reported for flame-retarded resins were measured according to the following standard tests.

Flammability: UL-94 vertical burning test in a flammability hood (according to UL); and Limiting oxygen index (LOI)(ASTM D 2863-77) on a FTA Flammability Unit Stanton Redcroft.

Izod notched impact energy: (ASTM D 256-81) on a Pendulum impact tester type 5102 Zwick.

Tensile impact energy: (ASTM D 1822-79) on a Pendulum impact tester type 5102 Zwick.

HDT: Deflection temperature under flexural load (18.5 $kg/cm^2$) (ASTM D 648-72) on a CEAST 6055.

U.V. Stability: Accelerated weathering test - irradiation for 250 hrs and measuring of the color change by color deviation, on an Accelerated Weathering Tester Q-U-V (B-lamps), (The Q-Panel Co.).

Color Deviation: Color measurement and comparison with reference specimen, on a Spectro Color Meter SCM-90, (Techno-Instruments Ltd.).

Preparation A (A1) To 15 g of a liquid polyester resin (410 brand, Fiberplast Ltd.) there were added eight drops of a 7% cobalt octoate solution and 12 drops of methyl ethyl ketone peroxide at ambient temperature. 2.4 g of tris(-pentabromobenzyl)isocyanurate (TPBB-IC) obtained in Example 1 were then added to this homogeneous solution with mixing. The mixture was quickly cast into a Teflon mould containing cavities of dimensions 6×100×3 mm. Curing was performed at ambient temperature for 24 hours and then in an oven at 150° C. for 3 hours. The specimens were removed and left to cool and the LOI (Limiting Oxygen Index) was measured and compared with that of an identically prepared sample not containing the flame-retardant compound of Example 1. The LOI of the TPBB-IC containing sample was 21.5, and that of the control specimen was 19.0.

(A2) A sample prepared as in A1 above, but substituting 2.4 g of poly(N-pentabromobenzyl-N', N"-tetrabromoxylylidene isocyanurate) of Example 5 for the TPBB-IC used in Preparation A1, yielded a cured polyester sample having an LOI of 21.3.

Preparation B

Acrylonitrile-butadiene-styrene (ex Borg-Warner, Grade MB) was made flame-retardant by the addition of 18.5 wt % of the compound of Example 1 (TPBB-IC), to give 14% bromine content. Another ABS sample was made flame-retarded by the additon of the well-known FR for ABS 1,2-bis(2,4,6-tribromophenoxy) ethane, known as FF-680 (ex Great Lakes Chemical Corp.), to give an identical 14% bromine content. The properties of the specimens so obtained were measured and compared, and the following results were obtained:

FF-680: UL94 (1.6 mm): V-0; HDT (° C.): 80; Izod Notched Impact (J/m): 49; DE after 250 hrs of UV irradiation: 47.

Ex. 5: UL94 (1.6 mm): V-0; HDT (° C.): 88.6; Izod Notched Impact (J/m): 44.1; DE after 250 hrs of UV irradiation: 42.

The above results show the improved properties of the compound of the invention, which possesses both higher HDT values and higher UV stability, which are both important properties for synthetic resins.

Preparation C

Two specimens of glass fiber reinforced polyethyleneterephtalate (PET GFR), containing 30% glass fiber (Petra 130, ex Allied Corporation) were prepared, one containing as the flame-retardant agent the compound of Example 1, and the other containing Pyrocheck-68 PB (Ferro Corporation), a brominated polystyrene containing 68.5% Br, together with antimony oxide (AO, Blue Star "RG", Campine). The FR agent contents employed were the minimal ones which provided a 1.6 mm thick specimen having a V-0 UL94 rating. The results obtained are shown in Table I below:

TABLE I

| Component (%) | Example 1 | Pyrocheck-68 |
|---|---|---|
| PET GFR (30% GF) | 90.85 | 85.3 |
| AO | 2.5 | 3.75 |
| Minimal % FR for V-0 | 6.65 | 10.95 |
| % Bromine | 5.0 | 7.5 |
| Maximal Processing temperature (°C.) | 330 | 310 |
| IZOD (295° C.) (J/m)(*) | 48.6 | 49.2 |
| IZOD (310° C.) (J/m)(*) | 53.3 | 50.3 |
| IZOD (330° C.) (J/m)(*) | 40.7 | |

(*)Value for specimen processed at given temperature

From the above data the advantages of the product of the invention, as compared with the well known FR Pyrocheck-68, can be seen. For instance, total amount of FR (organic FR and AO) required in order to obtained a UL94 V-0 rating is about 1.6 times less for the compound of Example 1. Additionally, it is possible to obtain higher temperatures (up to 330° C., instead of 310° C. with Pyrocheck), thereby more fully exploiting the glass fiber reinforcing.

The compounds of the invention possess unusually high thermal stability. For instance, the compound of Example 1 has a major TGA peak at 412° C., and that of Example 4 at 460° C. Thus such compounds can be used under the most demanding of high performance conditions. This surprisingly high thermal stability is also accompanied by other important characteristics, such as excellent UV stability of composition which incorporate them, and their unexpectedly high FR efficiency, with respect to the halogen content, as exemplified for instance in Composition C. In this illustrative composition, a loading of 40% less FR produced the same level of fire retardancy as that produced by the commercial FR Pyrocheck-68 PB. This fact does not only lead to a saving in material and cost, but more significantly the original properties of the resin are less influenced, since the amount of additive is less. Additionally, the Br content of some of the compounds of the invention, e.g., that of Example 5, may reach up to about 70% while conserving excellent thermal stability.

What we claim is:

1. A triazine derivative of the formula:

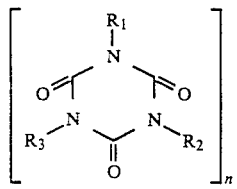

wherein $R_1$, $R_2$ and $R_3$ are independently selected from the group consisting of ring perhalogenated benzyls and ring perhalogenated xylylidenes, and n is an integer between 1 and 5.

2. The triazine derivative of claim 1, wherein $R_1$, $R_2$ and $R_3$ are independently selected from the group consisting of ring perhalogenated benzyls and n is 1.

3. The triazine derivative of claim 2, wherein $R_1$, $R_2$ and $R_3$ are independently selected from the group consisting of pentabromobenzyl and pentachlorobenzyl.

4. The triazine derivative of claim 3, wherein $R_1$, $R_2$ and $R_3$ are pentabromobenzyl.

5. The triazine derivative of claim 1, comprising poly(N-pentabromobenzyl-N'N''-tetrabromoxylylidene isocyanurate).

* * * * *

UNITED STATES PATENT AND TRADEMARK OFFICE
CERTIFICATE OF CORRECTION

PATENT NO. : 4,977,262

DATED : December 11, 1990

INVENTOR(S) : Herzlinger et al

It is certified that error appears in the above-identified patent and that said Letters Patent is hereby corrected as shown below:

Column 1, line 20, "trisubstitued" should read --trisubstituted--.

Column 3, line 33, "isocyanurate." should read --isocyanurate).--.

Column 3, lines 53-54, "isocyanurate." should read --isocyanurate).--.

Column 4, line 63, "(250 g; 0159 mol) should read --(250 g; 0.159 mol).--.

Column 6, line 8, "tetrabromoxylilydene" should read --tetrabromoxylylidene--.

Column 7, lines 19-20, "polyethyleneterephtalate" should read --polyethyleneterephthalate--.

Column 7, lines 47-48, "obtained" should read --obtain--.

Column 8, line 48, "-N'N"-" should read -- -N',N"- --.

Signed and Sealed this

Twenty-first Day of July, 1992

Attest:

DOUGLAS B. COMER

Attesting Officer    Acting Commissioner of Patents and Trademarks